US006469231B1

(12) United States Patent
Ek et al.

(10) Patent No.: US 6,469,231 B1
(45) Date of Patent: Oct. 22, 2002

(54) STARCH BRANCHING ENZYME II OF POTATO

(76) Inventors: Bo Ek, Nyhagen, S-740 30 Bjorklinge (SE); Jamshid Khosnoodi, Bandstolsvagen 3, 2 tr., S-756 48 Uppsala (SE); Clas-Tomas Larsson, Flogstavagen 55 B II, S-752 73 Uppsala (SE); Håkan Larsson, Hammarbygatan 58, S-753 24 Uppsala (SE); Lars Rask, Saves vag 14, S-752 63 Uppsala (SE)

( * ) Notice: Subject to any disclaimer, the term of this patent is extended or adjusted under 35 U.S.C. 154(b) by 0 days.

(21) Appl. No.: 09/658,499

(22) Filed: Sep. 8, 2000

Related U.S. Application Data

(62) Division of application No. 09/087,277, filed as application No. PCT/SE96/01558 on Nov. 28, 1996, now Pat. No. 6,169,226.

(30) Foreign Application Priority Data

Nov. 29, 1995 (SE) ............................................. 9504272
Apr. 19, 1996 (SE) ............................................. 9601506

(51) Int. Cl.[7] ........................ C12N 15/82; C12N 15/29; C12N 5/04; C12P 19/04; A01H 5/00

(52) U.S. Cl. ....................... 800/284; 800/278; 800/287; 800/317.2; 435/101; 435/320.1; 435/417; 435/419; 435/429; 435/468; 536/23.6

(58) Field of Search ......................... 536/23.6; 435/101, 435/320.1, 468, 417, 419, 429; 800/278, 284, 317.2, 287

(56) References Cited

FOREIGN PATENT DOCUMENTS

| | | |
|---|---|---|
| SE | 467160 | 6/1992 |
| WO | WO92/11376 | 7/1992 |
| WO | WO92/14827 | 9/1992 |
| WO | WO95/04826 | 2/1995 |
| WO | WO95/07355 | 3/1995 |
| WO | WO96/34968 | 11/1996 |

OTHER PUBLICATIONS

"Inhibition of the Expression of the Gene for Granule-–Bound Starch Synthase in Potato by Antisense Constructs" R.G.F. Visser et al., *MGG*, vol. 225 (1991) pp. 289–296.

"Approaches to Influence Starch Quantity and Starch Quality in Transgenic Plants", B. Muller et al., *Plant, Cell and Environment*, vol. 17 (1994) pp. 601–613.

"Starch Biosynthesis", Cathie Martin et al, *The Plant Cell*, vol. 7 (Jul. 1995) pp. 971–985.

"Cleavage of Structural Proteins During the Assembly of the Head of Bacteriophage T4", U.K. Laemmli, *Nature*, vol. 227, Aug. 15, 1970, pp. 680–685.

"Improved Method for the Isolation of RNA from Plant Tissues", Jurgen Logemann et al., *Analytical Biochemistry*, vol. 163 (1987) pp. 16–20.

"In–Gen Digestion of Proteins for Internal Sequence Analysis After One– or Two Dimensional Gel Electrophoresis", Jorge Rosenfeld et al., *Analytical Biochemistry*, vol. 203 (1992) pp. 173–179.

"Towards Modifying Plants for Altered Starch Content and Composition", Richard G.F. Visser et al., *TIBTECH*, vol. 11 (Feb. 1993) pp. 63–68.

Larsson et al, *Plant Mol. Biol.*, 37:505–511 (1998).

Larsson et al, *Plant Science*, 17:9–16 (1996).

Kuipers et al, *Euphytica*, 59:83–91 (1992).

Visser et al, *Plant Mol Biol.*, 17:691–699 (1991).

Flipse et al, *Planta*, 198:340–347 (1996).

Kossmann et al., *Mol. Gen. Genet.*, 230:39–44 (1991).

Jobling et al., *Plant J.*, 18(2):153–171 (1999).

Willmitzer et al, *Plant Polymeric Carbohydrates*, Jan. 7, 1993, pp. 33–39.

Kossmann et al, *Progress Biotechnol.*, 10:271–278 (1995).

Nakatani et al, *Jpn. J. Crop Science.*, 61 (3):463–468 (1992).

Burton et al, *Plant J.*, 7(1):3–15 (1995).

*Primary Examiner*—David T. Fox
(74) *Attorney, Agent, or Firm*—Burns, Doane, Swecker & Mathis, LLP

(57) ABSTRACT

The present invention relates to an amino acid sequence of second starch branching enzyme (SBE II) of potato and a fragment thereof as well as to the corresponding isolated DNA sequences. Furthermore, the invention relates to vectors comprising such an isolated DNA sequence, to processes for production of transgenic potatoes, and to the use of said potatoes for the production of starch. The starch obtained will show a changed pattern of branching of amylopectin as well as a changed amylose/amylopectin ratio.

11 Claims, 2 Drawing Sheets

FIG. 2

Peptide 1. EFGVWEIFLPN

Peptide 2. HGLQEFDRA

Peptide 3. ENDGIAAKADE

Peptide 4. YEIDPEI/LTN

SEQUENCE LISTING

```
<160> NUMBER OF SEQ ID NOS: 4

<210> SEQ ID NO 1
<211> LENGTH: 3074
<212> TYPE: DNA
<213> ORGANISM: Unknown
<220> FEATURE:
<223> OTHER INFORMATION: Description of Unknown Organism:beII gene
      (branching enzyme II) from Solanum tuberosum
      (potato)
<221> NAME/KEY: CDS
```

-continued

<222> LOCATION: (189)..(2825)
<221> NAME/KEY: sig_peptide
<222> LOCATION: (189)..(332)
<221> NAME/KEY: mat_peptide
<222> LOCATION: (333)..(2825)
<221> NAME/KEY: misc_feature
<222> LOCATION: (92)..(2156)
<223> OTHER INFORMATION: Nucleotides 92, 285, 1406, 1430, 1897 and 2156 are n wherein n = A, C, G or T.
<221> NAME/KEY: misc_feature
<222> LOCATION: (285)..(287)
<223> OTHER INFORMATION: Amino acid -16 is Xaa wherein Xaa = Ile, Leu, Val or Phe.
<221> NAME/KEY: misc_feature
<222> LOCATION: (1404)..(1406)
<223> OTHER INFORMATION: Amino acid 358 is Xaa wherein Xaa = Leu or Phe.
<221> NAME/KEY: misc_feature
<222> LOCATION: (1428)..(1430)
<223> OTHER INFORMATION: Amino acid 366 is Xaa wherein Xaa = Thr.
<221> NAME/KEY: misc_feature
<222> LOCATION: (1896)..(1898)
<223> OTHER INFORMATION: Amino acid 522 is Xaa wherein Xaa = Tyr, Ser, Cys or Phe.
<221> NAME/KEY: misc_feature
<222> LOCATION: (2154)..(2156)
<223> OTHER INFORMATION: Amino acid 608 is Xaa wherein Xaa = Pro.

<400> SEQUENCE: 1
aaacctcctc cactcagtct ttgtttctct ctctcttcac gcttctcttg gcgccttgaa 60
ctcagcaatt tgacactcag ttagttacac tnccatcact tatcagatct ctattttttc 120
tcttaattcc aaccaaggaa tgaataaaaa gatagatttg taaaaaccct aaggagagaa 180 gaagaaag atg gtg tat aca ctc tct gga gtt cgt ttt cct act gtt cca 230
Met Val Tyr Thr Leu Ser Gly Val Arg Phe Pro Thr Val Pro
-45 -40 -35 tca gtg tac aaa tct aat gga ttc agc agt aat ggt gat cgg agg aat 278
Ser Val Tyr Lys Ser Asn Gly Phe Ser Ser Asn Gly Asp Arg Arg Asn
-30 -25 -20 gct aat ntt tct gta ttc ttg aaa aag cac tct ctt tca cgg aag atc 326
Ala Asn Xaa Ser Val Phe Leu Lys Lys His Ser Leu Ser Arg Lys Ile
-15 -10 -5 ttg gct gaa aag tct tct tac aat tcc gaa tcc cga cct tct aca gtt 374
Leu Ala Glu Lys Ser Ser Tyr Asn Ser Glu Ser Arg Pro Ser Thr Val
-1 1 5 10 gca gca tcg ggg aaa gtc ctt gtg cct gga acc cag agt gat agc tcc 422
Ala Ala Ser Gly Lys Val Leu Val Pro Gly Thr Gln Ser Asp Ser Ser
15 20 25 30 tca tcc tca aca gac caa ttt gag ttc act gag aca tct cca gaa aat 470
Ser Ser Ser Thr Asp Gln Phe Glu Phe Thr Glu Thr Ser Pro Glu Asn
35 40 45 tcc cca gca tca act gat gta gat agt tca aca atg gaa cac gct agg 518
Ser Pro Ala Ser Thr Asp Val Asp Ser Ser Thr Met Glu His Ala Arg
50 55 60 cag att aaa act gag aac gat gac gtt gag ccg tca agt gat ctt aca 566
Gln Ile Lys Thr Glu Asn Asp Asp Val Glu Pro Ser Ser Asp Leu Thr
65 70 75 gga agt gtt gaa gag ctg gat ttt gct tca tca cta caa cta caa gaa 614
Gly Ser Val Glu Glu Leu Asp Phe Ala Ser Ser Leu Gln Leu Gln Glu
80 85 90 ggt ggt aaa ctg gag gag tct aaa aca tta aat act tct gaa gag aca 662
Gly Gly Lys Leu Glu Glu Ser Lys Thr Leu Asn Thr Ser Glu Glu Thr
95 100 105 110 att att gat gaa tct gat agg atc aga gag agg ggc atc cct cca cct 710
Ile Ile Asp Glu Ser Asp Arg Ile Arg Glu Arg Gly Ile Pro Pro Pro
115 120 125

-continued

```
gga ctt ggt cag aag att tat gaa ata gac ccc ctt ttg aca aac tat      758
Gly Leu Gly Gln Lys Ile Tyr Glu Ile Asp Pro Leu Leu Thr Asn Tyr
            130                 135                 140

cgt caa cac ctt gat tac agg tat tca cag tac aag aaa ctg agg gag      806
Arg Gln His Leu Asp Tyr Arg Tyr Ser Gln Tyr Lys Lys Leu Arg Glu
        145                 150                 155

gca att gac aag tat gag ggt ggt ttg gaa gct ttt tct cgt ggt tat      854
Ala Ile Asp Lys Tyr Glu Gly Gly Leu Glu Ala Phe Ser Arg Gly Tyr
    160                 165                 170

gaa aaa atg ggt ttc act cgt agt gct aca ggt atc act tac cgt gag      902
Glu Lys Met Gly Phe Thr Arg Ser Ala Thr Gly Ile Thr Tyr Arg Glu
175                 180                 185                 190

tgg gct cct ggt gcc cag tca gct gcc ctc att gga gat ttc aac aat      950
Trp Ala Pro Gly Ala Gln Ser Ala Ala Leu Ile Gly Asp Phe Asn Asn
                195                 200                 205

tgg gac gca aat gct gac att atg act cgg aat gaa ttt ggt gtc tgg      998
Trp Asp Ala Asn Ala Asp Ile Met Thr Arg Asn Glu Phe Gly Val Trp
            210                 215                 220

gag att ttt ctg cca aat aat gtg gat ggt tct cct gca att cct cat     1046
Glu Ile Phe Leu Pro Asn Asn Val Asp Gly Ser Pro Ala Ile Pro His
        225                 230                 235

ggg tcc aga gtg aag ata cgt atg gac act cca tca ggt gtt aag gat     1094
Gly Ser Arg Val Lys Ile Arg Met Asp Thr Pro Ser Gly Val Lys Asp
    240                 245                 250

tcc att cct gct tgg atc aac tac tct tta cag ctt cct gat gaa att     1142
Ser Ile Pro Ala Trp Ile Asn Tyr Ser Leu Gln Leu Pro Asp Glu Ile
255                 260                 265                 270

cca tat aat gga ata tat tat gat cca ccc gaa gag gag agg tat atc     1190
Pro Tyr Asn Gly Ile Tyr Tyr Asp Pro Pro Glu Glu Glu Arg Tyr Ile
                275                 280                 285

ttc caa cac cca cgg cca aag aaa cca aag tcg ctg aga ata tat gaa     1238
Phe Gln His Pro Arg Pro Lys Lys Pro Lys Ser Leu Arg Ile Tyr Glu
            290                 295                 300

tct cat att gga atg agt agt ccg gag cct aaa att aac tca tac gtg     1286
Ser His Ile Gly Met Ser Ser Pro Glu Pro Lys Ile Asn Ser Tyr Val
        305                 310                 315

aat ttt aga gat gaa gtt ctt cct cgc ata aaa aag ctt ggg tac aat     1334
Asn Phe Arg Asp Glu Val Leu Pro Arg Ile Lys Lys Leu Gly Tyr Asn
    320                 325                 330

gcg gtg caa att atg gct att caa gag cat tct tat tat gct agt ttt     1382
Ala Val Gln Ile Met Ala Ile Gln Glu His Ser Tyr Tyr Ala Ser Phe
335                 340                 345                 350

ggt tat cat gtc aca aat ttt ttn gca cca agc agc cgt ttt gga acn     1430
Gly Tyr His Val Thr Asn Phe Xaa Ala Pro Ser Ser Arg Phe Gly Xaa
                355                 360                 365

ccc gac gac ctt aag tct ttg att gat aaa gct cat gag cta gga att     1478
Pro Asp Asp Leu Lys Ser Leu Ile Asp Lys Ala His Glu Leu Gly Ile
            370                 375                 380

gtt gtt ctc atg gac att gtt cac agc cat gca tca aat aat act tta     1526
Val Val Leu Met Asp Ile Val His Ser His Ala Ser Asn Asn Thr Leu
        385                 390                 395

gat gga ctg aac atg ttt gac ggc aca gat agt tgt tac ttt cac tct     1574
Asp Gly Leu Asn Met Phe Asp Gly Thr Asp Ser Cys Tyr Phe His Ser
    400                 405                 410

gga gct cgt ggt tat cat tgg atg tgg gat tcc cgc ctc ttt aac tat     1622
Gly Ala Arg Gly Tyr His Trp Met Trp Asp Ser Arg Leu Phe Asn Tyr
415                 420                 425                 430

gga aac tgg gag gta ctt agg tat ctt ctc tca aat gcg aga tgg tgg     1670
Gly Asn Trp Glu Val Leu Arg Tyr Leu Leu Ser Asn Ala Arg Trp Trp
                435                 440                 445
```

-continued

```
ttg gat gag ttc aaa ttt gat gga ttt aga ttt gat ggt gtg aca tca     1718
Leu Asp Glu Phe Lys Phe Asp Gly Phe Arg Phe Asp Gly Val Thr Ser
            450                 455                 460

atg atg tat act cac cac gga tta tcg gtg gga ttc act ggg aac tac     1766
Met Met Tyr Thr His His Gly Leu Ser Val Gly Phe Thr Gly Asn Tyr
        465                 470                 475

gag gaa tac ttt gga ctc gca act gat gtg gat gct gtt gtg tat ctg     1814
Glu Glu Tyr Phe Gly Leu Ala Thr Asp Val Asp Ala Val Val Tyr Leu
    480                 485                 490

atg ctg gtc aac gat ctt att cat ggg ctt ttc cca gat gca att acc     1862
Met Leu Val Asn Asp Leu Ile His Gly Leu Phe Pro Asp Ala Ile Thr
495                 500                 505                 510

att ggt gaa gat gtt agc gga atg ccg aca ttt tnt att ccc gtt caa     1910
Ile Gly Glu Asp Val Ser Gly Met Pro Thr Phe Xaa Ile Pro Val Gln
                515                 520                 525

gat ggg ggt gtt ggc ttt gac tat cgg ctg cat atg gca att gct gat     1958
Asp Gly Gly Val Gly Phe Asp Tyr Arg Leu His Met Ala Ile Ala Asp
            530                 535                 540

aaa tgg att gag ttg ctc aag aaa cgg gat gag gat tgg aga gtg ggt     2006
Lys Trp Ile Glu Leu Leu Lys Lys Arg Asp Glu Asp Trp Arg Val Gly
        545                 550                 555

gat att gtt cat aca ctg aca aat aga aga tgg tcg gaa aag tgt gtt     2054
Asp Ile Val His Thr Leu Thr Asn Arg Arg Trp Ser Glu Lys Cys Val
    560                 565                 570

tca tac gct gaa agt cat gat caa gct cta gtc ggt gat aaa act ata     2102
Ser Tyr Ala Glu Ser His Asp Gln Ala Leu Val Gly Asp Lys Thr Ile
575                 580                 585                 590

gca ttc tgg ctg atg gag aag gat atg tat gat ttt atg gct ctg gat     2150
Ala Phe Trp Leu Met Glu Lys Asp Met Tyr Asp Phe Met Ala Leu Asp
                595                 600                 605

aga ccn tca aca tca tta ata gat cgt ggg ata gca ttg cac aag atg     2198
Arg Xaa Ser Thr Ser Leu Ile Asp Arg Gly Ile Ala Leu His Lys Met
            610                 615                 620

att agg ctt gta act atg gga tta gga gga gaa ggg tac cta aat ttc     2246
Ile Arg Leu Val Thr Met Gly Leu Gly Gly Glu Gly Tyr Leu Asn Phe
        625                 630                 635

atg gga aat gaa ttc ggc cac cct gag tgg att gat ttc cct agg gct     2294
Met Gly Asn Glu Phe Gly His Pro Glu Trp Ile Asp Phe Pro Arg Ala
    640                 645                 650

gaa caa cac ctc tct gat ggc tca gta att ccc gga aac caa ttc agt     2342
Glu Gln His Leu Ser Asp Gly Ser Val Ile Pro Gly Asn Gln Phe Ser
655                 660                 665                 670

tat gat aaa tgc aga cgg aga ttt gac ctg gga gat gca gaa tat tta     2390
Tyr Asp Lys Cys Arg Arg Arg Phe Asp Leu Gly Asp Ala Glu Tyr Leu
                675                 680                 685

aga tac cgt ggg ttg caa gaa ttt gac cgg gct atg cag tat ctt gaa     2438
Arg Tyr Arg Gly Leu Gln Glu Phe Asp Arg Ala Met Gln Tyr Leu Glu
            690                 695                 700

gat aaa tat gag ttt atg act tca gaa cac cag ttc ata tca cga aag     2486
Asp Lys Tyr Glu Phe Met Thr Ser Glu His Gln Phe Ile Ser Arg Lys
        705                 710                 715

gat gaa gga gat agg atg att gta ttt gaa aaa gga aac cta gtt ttt     2534
Asp Glu Gly Asp Arg Met Ile Val Phe Glu Lys Gly Asn Leu Val Phe
    720                 725                 730

gtc ttt aat ttt cac tgg aca aaa agc tat tca gac tat cgc ata ggc     2582
Val Phe Asn Phe His Trp Thr Lys Ser Tyr Ser Asp Tyr Arg Ile Gly
735                 740                 745                 750

tgc ctg aag cct gga aaa tac aag gtt gcc ttg gac tca gat gat cca     2630
Cys Leu Lys Pro Gly Lys Tyr Lys Val Ala Leu Asp Ser Asp Asp Pro
```

-continued

```
                755                 760                 765

ctt ttt ggt ggc ttc ggg aga att gat cat aat gcc gaa tat ttc acc     2678
Leu Phe Gly Gly Phe Gly Arg Ile Asp His Asn Ala Glu Tyr Phe Thr
            770                 775                 780

ttt gaa gga tgg tat gat gat cgt cct cgt tca att atg gtg tat gca     2726
Phe Glu Gly Trp Tyr Asp Asp Arg Pro Arg Ser Ile Met Val Tyr Ala
        785                 790                 795

cct agt aga aca gca gtg gtc tat gca cta gta gac aaa gaa gaa gaa     2774
Pro Ser Arg Thr Ala Val Val Tyr Ala Leu Val Asp Lys Glu Glu Glu
    800                 805                 810

gaa gaa gaa gaa gta gca gta gta gaa gaa gta gta gta gaa gaa gaa     2822
Glu Glu Glu Glu Val Ala Val Val Glu Glu Val Val Val Glu Glu Glu
815                 820                 825                 830

tga acgaacttgt gatcgcgttg aaagatttga aggctacata gagcttcttg         2875

acgtatctgg caatattgca tcagtcttgg cggaatttca tgtgacaaaa ggtttgcaat   2935

tctttccact attagtagtg caacgatata cgcagagatg aagtgctgca caaacatatg   2995

taaaatcgat gaatttatgt cgaatgctgg gacgggcttc agcaggtttt gcttagtgag   3055

ttctgtaaat tgtcatctc                                                3074


<210> SEQ ID NO 2
<211> LENGTH: 878
<212> TYPE: PRT
<213> ORGANISM: Unknown
<220> FEATURE:
<223> OTHER INFORMATION: Description of Unknown Organism:beII gene
      (branching enzyme II) from Solanum tuberosum (potato)

<400> SEQUENCE: 2

Met Val Tyr Thr Leu Ser Gly Val Arg Phe Pro Thr Val Pro Ser Val
  1               5                  10                  15

Tyr Lys Ser Asn Gly Phe Ser Ser Asn Gly Asp Arg Arg Asn Ala Asn
            20                  25                  30

Xaa Ser Val Phe Leu Lys Lys His Ser Leu Ser Arg Lys Ile Leu Ala
        35                  40                  45

Glu Lys Ser Ser Tyr Asn Ser Glu Ser Arg Pro Ser Thr Val Ala Ala
     50                  55                  60

Ser Gly Lys Val Leu Val Pro Gly Thr Gln Ser Asp Ser Ser Ser Ser
 65                  70                  75                  80

Ser Thr Asp Gln Phe Glu Phe Thr Glu Thr Ser Pro Glu Asn Ser Pro
                85                  90                  95

Ala Ser Thr Asp Val Asp Ser Ser Thr Met Glu His Ala Arg Gln Ile
            100                 105                 110

Lys Thr Glu Asn Asp Asp Val Glu Pro Ser Ser Asp Leu Thr Gly Ser
        115                 120                 125

Val Glu Glu Leu Asp Phe Ala Ser Ser Leu Gln Leu Gln Glu Gly Gly
    130                 135                 140

Lys Leu Glu Glu Ser Lys Thr Leu Asn Thr Ser Glu Glu Thr Ile Ile
145                 150                 155                 160

Asp Glu Ser Asp Arg Ile Arg Glu Arg Gly Ile Pro Pro Pro Gly Leu
                165                 170                 175

Gly Gln Lys Ile Tyr Glu Ile Asp Pro Leu Leu Thr Asn Tyr Arg Gln
            180                 185                 190

His Leu Asp Tyr Arg Tyr Ser Gln Tyr Lys Lys Leu Arg Glu Ala Ile
        195                 200                 205

Asp Lys Tyr Glu Gly Gly Leu Glu Ala Phe Ser Arg Gly Tyr Glu Lys
```

-continued

```
    210                 215                 220

Met Gly Phe Thr Arg Ser Ala Thr Gly Ile Thr Tyr Arg Glu Trp Ala
225                 230                 235                 240

Pro Gly Ala Gln Ser Ala Ala Leu Ile Gly Asp Phe Asn Asn Trp Asp
                245                 250                 255

Ala Asn Ala Asp Ile Met Thr Arg Asn Glu Phe Gly Val Trp Glu Ile
            260                 265                 270

Phe Leu Pro Asn Asn Val Asp Gly Ser Pro Ala Ile Pro His Gly Ser
        275                 280                 285

Arg Val Lys Ile Arg Met Asp Thr Pro Ser Gly Val Lys Asp Ser Ile
    290                 295                 300

Pro Ala Trp Ile Asn Tyr Ser Leu Gln Leu Pro Asp Glu Ile Pro Tyr
305                 310                 315                 320

Asn Gly Ile Tyr Tyr Asp Pro Pro Glu Glu Glu Arg Tyr Ile Phe Gln
                325                 330                 335

His Pro Arg Pro Lys Lys Pro Lys Ser Leu Arg Ile Tyr Glu Ser His
            340                 345                 350

Ile Gly Met Ser Ser Pro Glu Pro Lys Ile Asn Ser Tyr Val Asn Phe
        355                 360                 365

Arg Asp Glu Val Leu Pro Arg Ile Lys Lys Leu Gly Tyr Asn Ala Val
    370                 375                 380

Gln Ile Met Ala Ile Gln Glu His Ser Tyr Tyr Ala Ser Phe Gly Tyr
385                 390                 395                 400

His Val Thr Asn Phe Xaa Ala Pro Ser Ser Arg Phe Gly Xaa Pro Asp
                405                 410                 415

Asp Leu Lys Ser Leu Ile Asp Lys Ala His Glu Leu Gly Ile Val Val
            420                 425                 430

Leu Met Asp Ile Val His Ser His Ala Ser Asn Asn Thr Leu Asp Gly
        435                 440                 445

Leu Asn Met Phe Asp Gly Thr Asp Ser Cys Tyr Phe His Ser Gly Ala
    450                 455                 460

Arg Gly Tyr His Trp Met Trp Asp Ser Arg Leu Phe Asn Tyr Gly Asn
465                 470                 475                 480

Trp Glu Val Leu Arg Tyr Leu Leu Ser Asn Ala Arg Trp Trp Leu Asp
                485                 490                 495

Glu Phe Lys Phe Asp Gly Phe Arg Phe Asp Gly Val Thr Ser Met Met
            500                 505                 510

Tyr Thr His His Gly Leu Ser Val Gly Phe Thr Gly Asn Tyr Glu Glu
        515                 520                 525

Tyr Phe Gly Leu Ala Thr Asp Val Asp Ala Val Val Tyr Leu Met Leu
    530                 535                 540

Val Asn Asp Leu Ile His Gly Leu Phe Pro Asp Ala Ile Thr Ile Gly
545                 550                 555                 560

Glu Asp Val Ser Gly Met Pro Thr Phe Xaa Ile Pro Val Gln Asp Gly
                565                 570                 575

Gly Val Gly Phe Asp Tyr Arg Leu His Met Ala Ile Ala Asp Lys Trp
            580                 585                 590

Ile Glu Leu Leu Lys Lys Arg Asp Glu Asp Trp Arg Val Gly Asp Ile
        595                 600                 605

Val His Thr Leu Thr Asn Arg Arg Trp Ser Glu Lys Cys Val Ser Tyr
    610                 615                 620

Ala Glu Ser His Asp Gln Ala Leu Val Gly Asp Lys Thr Ile Ala Phe
625                 630                 635                 640
```

-continued

```
Trp Leu Met Glu Lys Asp Met Tyr Asp Phe Met Ala Leu Asp Arg Xaa
                645                 650                 655

Ser Thr Ser Leu Ile Asp Arg Gly Ile Ala Leu His Lys Met Ile Arg
            660                 665                 670

Leu Val Thr Met Gly Leu Gly Gly Glu Gly Tyr Leu Asn Phe Met Gly
        675                 680                 685

Asn Glu Phe Gly His Pro Glu Trp Ile Asp Phe Pro Arg Ala Glu Gln
    690                 695                 700

His Leu Ser Asp Gly Ser Val Ile Pro Gly Asn Gln Phe Ser Tyr Asp
705                 710                 715                 720

Lys Cys Arg Arg Arg Phe Asp Leu Gly Asp Ala Glu Tyr Leu Arg Tyr
                725                 730                 735

Arg Gly Leu Gln Glu Phe Asp Arg Ala Met Gln Tyr Leu Glu Asp Lys
            740                 745                 750

Tyr Glu Phe Met Thr Ser Glu His Gln Phe Ile Ser Arg Lys Asp Glu
        755                 760                 765

Gly Asp Arg Met Ile Val Phe Glu Lys Gly Asn Leu Val Phe Val Phe
    770                 775                 780

Asn Phe His Trp Thr Lys Ser Tyr Ser Asp Tyr Arg Ile Gly Cys Leu
785                 790                 795                 800

Lys Pro Gly Lys Tyr Lys Val Ala Leu Asp Ser Asp Asp Pro Leu Phe
                805                 810                 815

Gly Gly Phe Gly Arg Ile Asp His Asn Ala Glu Tyr Phe Thr Phe Glu
            820                 825                 830

Gly Trp Tyr Asp Asp Arg Pro Arg Ser Ile Met Val Tyr Ala Pro Ser
        835                 840                 845

Arg Thr Ala Val Val Tyr Ala Leu Val Asp Lys Glu Glu Glu Glu Glu
    850                 855                 860

Glu Glu Val Ala Val Val Glu Glu Val Val Val Glu Glu Glu
865                 870                 875


<210> SEQ ID NO 3
<211> LENGTH: 1393
<212> TYPE: DNA
<213> ORGANISM: Unknown
<220> FEATURE:
<223> OTHER INFORMATION: Description of Unknown Organism:beII gene
      fragment (branching enzyme II) from Solanum tuberosum
      (potato)
<221> NAME/KEY: CDS
<222> LOCATION: (2)..(1393)
<221> NAME/KEY: misc_feature
<222> LOCATION: (424)..(1150)
<223> OTHER INFORMATION: Nucleotides 424, 891 and 1150 are n wherein
      n = A, C, G or T.
<221> NAME/KEY: misc_feature
<222> LOCATION: (422)..(424)
<223> OTHER INFORMATION: Amino acid 141 is Xaa wherein Xaa = Thr.
<221> NAME/KEY: misc_feature
<222> LOCATION: (890)..(892)
<223> OTHER INFORMATION: Amino acid 297 is Xaa wherein Xaa = Tyr, Ser,
      Cys or Phe.
<221> NAME/KEY: misc_feature
<222> LOCATION: (1148)..(1150)
<223> OTHER INFORMATION: Amino acid 383 is Xaa wherein Xaa = Pro.

<400> SEQUENCE: 3

t ctg cca aat aat gtg gat ggt tct cct gca att cct cat ggg tcc aga      49
  Leu Pro Asn Asn Val Asp Gly Ser Pro Ala Ile Pro His Gly Ser Arg
    1               5                  10                  15

gtg aag ata cgt atg gac act cca tca ggt gtt aag gat tcc att cct       97
```

-continued

```
Val Lys Ile Arg Met Asp Thr Pro Ser Gly Val Lys Asp Ser Ile Pro
            20                  25                  30

gct tgg atc aac tac tct tta cag ctt cct gat gaa att cca tat aat      145
Ala Trp Ile Asn Tyr Ser Leu Gln Leu Pro Asp Glu Ile Pro Tyr Asn
        35                  40                  45

gga ata tat tat gat cca ccc gaa gag gag agg tat atc ttc caa cac      193
Gly Ile Tyr Tyr Asp Pro Pro Glu Glu Glu Arg Tyr Ile Phe Gln His
    50                  55                  60

cca cgg cca aag aaa cca aag tcg ctg aga ata tat gaa tct cat att      241
Pro Arg Pro Lys Lys Pro Lys Ser Leu Arg Ile Tyr Glu Ser His Ile
 65                  70                  75                  80

gga atg agt agt ccg gag cct aaa att aac tca tac gtg aat ttt aga      289
Gly Met Ser Ser Pro Glu Pro Lys Ile Asn Ser Tyr Val Asn Phe Arg
                85                  90                  95

gat gaa gtt ctt cct cgc ata aaa aag ctt ggg tac aat gcg gtg caa      337
Asp Glu Val Leu Pro Arg Ile Lys Lys Leu Gly Tyr Asn Ala Val Gln
            100                 105                 110

att atg gct att caa gag cat tct tat tat gct agt ttt ggt tat cat      385
Ile Met Ala Ile Gln Glu His Ser Tyr Tyr Ala Ser Phe Gly Tyr His
        115                 120                 125

gtc aca aat ttt ttn gca cca agc agc cgt ttt gaa acn ccc gac gac      433
Val Thr Asn Phe Xaa Ala Pro Ser Ser Arg Phe Glu Xaa Pro Asp Asp
    130                 135                 140

ctt aag tct ttg att gat aaa gct cat gag cta gga att gtt gtt ctc      481
Leu Lys Ser Leu Ile Asp Lys Ala His Glu Leu Gly Ile Val Val Leu
145                 150                 155                 160

atg gac att gtt cac agc cat gca tca aat aat act tta gat gga ctg      529
Met Asp Ile Val His Ser His Ala Ser Asn Asn Thr Leu Asp Gly Leu
                165                 170                 175

aac atg ttt gac ggc aca gat agt tgt tac ttt cac tct gga gct cgt      577
Asn Met Phe Asp Gly Thr Asp Ser Cys Tyr Phe His Ser Gly Ala Arg
            180                 185                 190

ggt tat cat tgg atg tgg gat tcc cgc ctc ttt aac tat gga aac tgg      625
Gly Tyr His Trp Met Trp Asp Ser Arg Leu Phe Asn Tyr Gly Asn Trp
        195                 200                 205

gag gta ctt agg tat ctt ctc tca aat gcg aga tgg tgg ttg gat gag      673
Glu Val Leu Arg Tyr Leu Leu Ser Asn Ala Arg Trp Trp Leu Asp Glu
    210                 215                 220

ttc aaa ttt gat gga ttt aga ttt gat ggt gtg aca tca atg atg tat      721
Phe Lys Phe Asp Gly Phe Arg Phe Asp Gly Val Thr Ser Met Met Tyr
225                 230                 235                 240

act cac cac gga tta tcg gtg gga ttc act ggg aac tac gag gaa tac      769
Thr His His Gly Leu Ser Val Gly Phe Thr Gly Asn Tyr Glu Glu Tyr
                245                 250                 255

ttt gga ctc gca act gat gtg gat gct gtt gtg tat ctg atg ctg gtc      817
Phe Gly Leu Ala Thr Asp Val Asp Ala Val Val Tyr Leu Met Leu Val
            260                 265                 270

aac gat ctt att cat ggg ctt ttc cca gat gca att acc att ggt gaa      865
Asn Asp Leu Ile His Gly Leu Phe Pro Asp Ala Ile Thr Ile Gly Glu
        275                 280                 285

gat gtt agc gga atg ccg aca ttt tnt att ccc gtt caa gat ggg ggt      913
Asp Val Ser Gly Met Pro Thr Phe Xaa Ile Pro Val Gln Asp Gly Gly
    290                 295                 300

gtt ggc ttt gac tat cgg ctg cat atg gca att gct gat aaa tgg att      961
Val Gly Phe Asp Tyr Arg Leu His Met Ala Ile Ala Asp Lys Trp Ile
305                 310                 315                 320

gag ttg ctc aag aaa cgg gat gag gat tgg aga gtg ggt gat att gtt     1009
Glu Leu Leu Lys Lys Arg Asp Glu Asp Trp Arg Val Gly Asp Ile Val
                325                 330                 335
```

-continued

```
cat aca ctg aca aat aga aga tgg tcg gaa aag tgt gtt tca tac gct     1057
His Thr Leu Thr Asn Arg Arg Trp Ser Glu Lys Cys Val Ser Tyr Ala
            340                 345                 350

gaa agt cat gat caa gct cta gtc ggt gat aaa act ata gca ttc tgg     1105
Glu Ser His Asp Gln Ala Leu Val Gly Asp Lys Thr Ile Ala Phe Trp
        355                 360                 365

ctg atg gac aag gat atg tat gat ttt atg gct ctg gat aga ccn tca     1153
Leu Met Asp Lys Asp Met Tyr Asp Phe Met Ala Leu Asp Arg Xaa Ser
    370                 375                 380

aca tca tta ata gat cgt ggg ata gca ttg cac aag atg att agg ctt     1201
Thr Ser Leu Ile Asp Arg Gly Ile Ala Leu His Lys Met Ile Arg Leu
385                 390                 395                 400

gta act atg gga tta gga gga gaa ggg tac cta aat ttc atg gga aat     1249
Val Thr Met Gly Leu Gly Gly Glu Gly Tyr Leu Asn Phe Met Gly Asn
                405                 410                 415

gaa ttc ggc cac cct gag tgg att gat ttc cct agg gct gaa caa cac     1297
Glu Phe Gly His Pro Glu Trp Ile Asp Phe Pro Arg Ala Glu Gln His
            420                 425                 430

ctc tct gat ggc tca gta att ccc gga aac caa ttc agt tat gat aaa     1345
Leu Ser Asp Gly Ser Val Ile Pro Gly Asn Gln Phe Ser Tyr Asp Lys
        435                 440                 445

tgc aga cgg aga ttt gac ctg gga gat gca gaa tat tta aga tac cgt     1393
Cys Arg Arg Arg Phe Asp Leu Gly Asp Ala Glu Tyr Leu Arg Tyr Arg
    450                 455                 460


<210> SEQ ID NO 4
<211> LENGTH: 464
<212> TYPE: PRT
<213> ORGANISM: Unknown
<220> FEATURE:
<223> OTHER INFORMATION: Description of Unknown Organism:beII gene
      fragment (branching enzyme II) from Solanum tuberosum (potato)

<400> SEQUENCE: 4

Leu Pro Asn Asn Val Asp Gly Ser Pro Ala Ile Pro His Gly Ser Arg
  1               5                  10                  15

Val Lys Ile Arg Met Asp Thr Pro Ser Gly Val Lys Asp Ser Ile Pro
             20                  25                  30

Ala Trp Ile Asn Tyr Ser Leu Gln Leu Pro Asp Glu Ile Pro Tyr Asn
         35                  40                  45

Gly Ile Tyr Tyr Asp Pro Pro Glu Glu Glu Arg Tyr Ile Phe Gln His
     50                  55                  60

Pro Arg Pro Lys Lys Pro Lys Ser Leu Arg Ile Tyr Glu Ser His Ile
 65                  70                  75                  80

Gly Met Ser Ser Pro Glu Pro Lys Ile Asn Ser Tyr Val Asn Phe Arg
                 85                  90                  95

Asp Glu Val Leu Pro Arg Ile Lys Lys Leu Gly Tyr Asn Ala Val Gln
            100                 105                 110

Ile Met Ala Ile Gln Glu His Ser Tyr Tyr Ala Ser Phe Gly Tyr His
        115                 120                 125

Val Thr Asn Phe Xaa Ala Pro Ser Ser Arg Phe Glu Xaa Pro Asp Asp
    130                 135                 140

Leu Lys Ser Leu Ile Asp Lys Ala His Glu Leu Gly Ile Val Val Leu
145                 150                 155                 160

Met Asp Ile Val His Ser His Ala Ser Asn Asn Thr Leu Asp Gly Leu
                165                 170                 175

Asn Met Phe Asp Gly Thr Asp Ser Cys Tyr Phe His Ser Gly Ala Arg
            180                 185                 190
```

-continued

```
Gly Tyr His Trp Met Trp Asp Ser Arg Leu Phe Asn Tyr Gly Asn Trp
        195                 200                 205

Glu Val Leu Arg Tyr Leu Leu Ser Asn Ala Arg Trp Trp Leu Asp Glu
    210                 215                 220

Phe Lys Phe Asp Gly Phe Arg Phe Asp Gly Val Thr Ser Met Met Tyr
225                 230                 235                 240

Thr His His Gly Leu Ser Val Gly Phe Thr Gly Asn Tyr Glu Glu Tyr
                245                 250                 255

Phe Gly Leu Ala Thr Asp Val Asp Ala Val Val Tyr Leu Met Leu Val
            260                 265                 270

Asn Asp Leu Ile His Gly Leu Phe Pro Asp Ala Ile Thr Ile Gly Glu
        275                 280                 285

Asp Val Ser Gly Met Pro Thr Phe Xaa Ile Pro Val Gln Asp Gly Gly
    290                 295                 300

Val Gly Phe Asp Tyr Arg Leu His Met Ala Ile Ala Asp Lys Trp Ile
305                 310                 315                 320

Glu Leu Leu Lys Lys Arg Asp Glu Asp Trp Arg Val Gly Asp Ile Val
                325                 330                 335

His Thr Leu Thr Asn Arg Arg Trp Ser Glu Lys Cys Val Ser Tyr Ala
            340                 345                 350

Glu Ser His Asp Gln Ala Leu Val Gly Asp Lys Thr Ile Ala Phe Trp
        355                 360                 365

Leu Met Asp Lys Asp Met Tyr Asp Phe Met Ala Leu Asp Arg Xaa Ser
    370                 375                 380

Thr Ser Leu Ile Asp Arg Gly Ile Ala Leu His Lys Met Ile Arg Leu
385                 390                 395                 400

Val Thr Met Gly Leu Gly Gly Glu Gly Tyr Leu Asn Phe Met Gly Asn
                405                 410                 415

Glu Phe Gly His Pro Glu Trp Ile Asp Phe Pro Arg Ala Glu Gln His
            420                 425                 430

Leu Ser Asp Gly Ser Val Ile Pro Gly Asn Gln Phe Ser Tyr Asp Lys
        435                 440                 445

Cys Arg Arg Arg Phe Asp Leu Gly Asp Ala Glu Tyr Leu Arg Tyr Arg
    450                 455                 460
```

STARCH BRANCHING ENZYME II OF POTATO

This application is a divisional of U.S. patent application Ser. No. 09/087,277, filed May 29, 1998, now U.S. Pat. No. 6,169,226, which is a continuation of International Application No. PCT/SE96/01558, filed Nov. 28, 1996 that designates the United States.

FIELD OF THE INVENTION

The present invention relates to a novel starch branching enzyme of potato. More specifically, the present invention relates to an amino acid sequence of a second starch branching enzyme (SBE II) of potato and a fragment thereof as well as their corresponding DNA sequences. Furthermore, the invention relates to vectors comprising such DNA sequences, to processes for production of transgenic potatoes, and to the use of said potatoes for the production of starch.

Starch is a complex mixture of different molecule forms differing in degree of polymerization and branching of the glucose chains. Starch consists of amylose and amylopectin, whereby the amylose consists of an essentially linear α-1,4-glucan and amylopectin consists of α-1,4-glucans connected to each other via α-1,6-linkages and, thus, forming a branched polyglucan. Thus, starch is not a uniform raw material.

Starch is synthesized via at least three enzymatic reactions in which ADP glucose phosphorylase (EC 2.7.7.27), starch synthase (EC 2.4.1.21) and starch branching enzyme (EC 2.4.1.18) are involved. Starch branching enzyme (SBE, also called Q-enzyme) is believed to have two different enzymatic activities. It catalyzes both the hydrolysis of α-1,4-glucosidic bonds and the formation of α-1,6-glucosidic bonds during synthesis of the branched component in starch, i.e. amylopectin.

Plant starch is a valuable source of renewable raw material used in, for example, the chemical industry (Visser and Jacobsen, 1993). However, the quality of the starch has to meet the demands of the processing industry wherein uniformity of structure is an important criterion. For industrial application there is a need of plants only containing amylose starch and plants only containing amylopectin starch, respectively.

Processes for altering the amylose/amylopectin ratio in starch have already been proposed. For example, in WO95/04826 there is described DNA sequences encoding debranching enzymes with the ability to reduce or increase the degree of branching of amylopectin in transgenic plants, e.g. potatoes.

In WO92/14827 plasmids are described having DNA sequences that after insertion into the genome of the plants cause changes in the carbohydrate concentration and the carbohydrate composition in regenerated plants. These changes can be obtained from a sequence of a branching enzyme that is located on these plasmids. This branching enzyme is proposed to alter the amylose/amylopectin ratio in starch of the plants, especially in commercially used plants.

WO92/14827 describes the only hitherto known starch branching enzyme in potato and within the art it is not known whether other starch branching enzymes are involved in the synthesis of branched starch of potato.

In Mol Gen Genet (1991) 225:289–296(Visser et al., there is described inhibition of the expression of the gene for granule-bound starch synthase in potato by antisense constructs. Inhibition of the enzyme in potato tuber starch was up to 100% in which case amylose-free starch was provided.

However, the prior known methods for inhibiting amylopectin have not been that successful and, therefore, alternative methods for inhibiting amylopectin are still highly desirable (Müller-Röber and Koβmann, 1994; Martin and Smith, 1995).

SUMMARY OF THE INVENTION

The object of the present invention is to enable altering the degree of amylopectin branching and the amylopectin/amylose ratio in potato starch.

According to the present invention this object is achieved by providing a novel isolated DNA sequence encoding a second starch branching enzyme, SBE II, and fragments thereof, which after insertion into the genome of the plants cause changes in said branching degree and ratio in regenerated plants.

Within the scope of the present invention there is also included the amino acid sequence of SBE II and fragments thereof.

Also variants of the above DNA sequence resulting from the degeneracy of the genetic code are encompassed.

The novel DNA sequence encoding SBEII, comprising 3074 nucleotides, as well as the corresponding amino acid sequence comprising 878 amino acids, are shown in SEQ ID No. 1. One 1393 nucleotides long fragment of the above DNA sequence, corresponding to nucleotides 1007 to 2399 of the DNA sequence in SEQ ID No. 1, as well as the corresponding amino acid sequence comprising 464 amino acids, are shown in SEQ ID No. 2.

Furthermore, there are provided vectors comprising said isolated DNA-sequences and regulatory elements active in potato. The DNA sequences may be inserted in the sense or antisense (reversed) orientation in the vectors in relation to a promoter immediately upstream from the DNA sequence.

Also there is provided a process for the production of transgenic potatoes with a reduced degree of branching of amylopectin starch, comprising the following steps:

a) transfer and incorporation of a vector according to the invention into the genome of a potato cell, and b) regeneration of intact, whole plants from the transformed cells.

Finally, the invention provides the use of said transgenic potatoes for the production of starch.

The invention will be described in more detail below in association with an experimental part and the accompanying drawings.

BRIEF DESCRIPTION OF THE DRAWINGS

FIG. 2 shows 4 peptide sequences derived from digested proteins from potato tuber starch.

DETAILED DESCRIPTION OF THE INVENTION

Isolation of Starch from Potato Tubers

Figure 1:
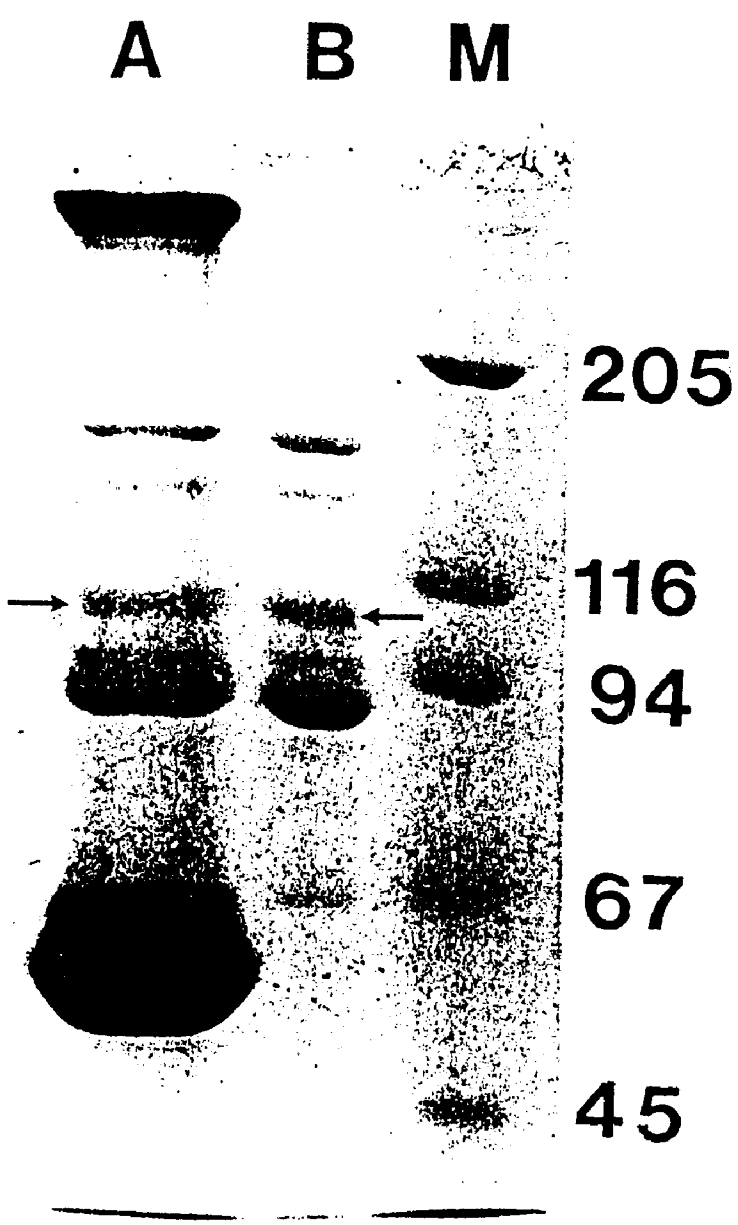
FIG. 1 shows SDS polyacrylamide electrophoresis of proteins extracted from starch of normal potato (lane A) and transgenic potato (lane B). Excised protein bands are marked with arrows. Lane M: Molecular weight marker proteins (kDa).

Potato plants (*Solanum tuberosum*) were grown in the field. Peeled tubers from either cv. Early Puritan or from a transgenic potato line essentially lacking granule-bound starch synthase I (Svalöf Weibull AB, international application number PCT/SE91/00892), were homogenized at 4° C. in a fruit juicer. To the “juice fraction”, which contained a large fraction of the starch, was immediately added Tris-HCl, pH 7.5, to 50 mM, Na-dithionite to 30 mM and ethylenedinitrilotetraacetic acid (EDTA) to 10 mM. The starch granules were allowed to sediment for 30 min and washed 4× with 10 bed volumes of washing buffer (50 mM Tris-Hcl, pH 7.5, 10 mM EDTA). The starch, which was left on the bench at +4° C. for 30 min to sediment between every wash, was finally washed with 3×3 bed volumes of acetone, air dried over night, and stored at −20° C.

Extraction of Proteins from Tuber Starch

Stored starch (20 g) was continuously mixed with 200 ml extraction buffer (50 mM Tris-HCl, pH 7.5, 2% (w/v) sodium dodecyl sulfate (SDS), 5 mM EDTA) by aspiration with a pipette at 85° C. until the starch was gelatinized. The samples were then frozen at −70° C. for 1 hour. After thawing at 50° C., the samples were centrifuged for 20 min at 12,000×g at 10° C. The supernatants were collected and re-centrifuged at 3,000×g for 15 min. The final supernatants were filtered through 0.45$\mu$ filters and 2.25 volumes of ice-cold acetone were added. After 30 min incubation at 4° C., the protein precipitates were collected by centrifugation (3,000×g for 30 min at 4° C.), and dissolved in 50 Mm Tris-HCl, pH 7.5. An aliquot of each preparation was analyzed by SDS poly-acrylamide gel electrophoresis according to Laemmli (1970)(FIG. 1). The proteins in the remaining portions of the preparations were concentrated by precipitation with trichloroacetic acid (10%) and the proteins were separated on an 8% SDS polyacrylamide gel Laemmli, (1970). The proteins in the gel were stained with Coomassie Brilliant Blue R-250 (0.2% in 20% methanol, 0.5% acetic acid, 79.5% $H_2O$).

In Gel Digestion and Sequencing of Peptides

The stained bands marked with arrows in FIG. 1 corresponding to an apparent molecular weight of about 100 kDa were excised and washed twice with 0.2M $NH_4HCO_3$ in 50% acetonitrile under continuous stirring at 35° C. for 20 min. After each washing, the liquid was removed and the gel pieces were allowed to dry by evaporation in a fume hood. The completely dried gel pieces were then separately placed on parafilm and 2 $\mu$l of 0.2M $NH_4CO_3$, 0.02% Tween-20 were added. Modified trypsin (Promega, Madison, Wis., U.S.A) (0.25 $\mu$g in 2 $\mu$l) was sucked into the gel pieces whereafter 0.2M $NH_4CO_3$ was added in 5 $\mu$l portions until they had resumed their original sizes. The gel slices were further divided into three pieces and transferred to an Eppendorf tube. 0.2M $NH_4CO_3$ (200 $\mu$l) was added and the proteins contained in the gel pieces were digested over night at 37° C. (Rosenfeld et al. 1992). After completed digestion, trifluoroacetic acid was added to 1% and the supernatants removed and saved. The gel pieces were further extracted twice with 60% acetonitrile, 0.1% tri-fluoroacetic acid (200 $\mu$l) under continuous shaking at 37° C. for 20 min. The two supernatants from these extractions were combined with the first supernatant. The gel pieces were finally washed with 60% acetonitrile, 0.1% trifluoroacetic acid, 0.02% Tween-20 (200 $\mu$l). Also these supernatants were combined with the other supernatants and the volume was reduced to 50 $\mu$l by evaporation. The extracted peptides were separated on a SMART® chromatography system (Pharmacia, Uppsala, Sweden) equipped with a $\mu$RPC C2/C18 SC2.1/10 column. Peptides were eluted with a gradient of 0–60% acetonitrile in water/0.1% trifluoroacetic acid over 60 min with a flow rate of 100 $\mu$l/min. Peptides were sequenced either on an Applied Biosystems 470A gas phase sequenator with an on line PTH-amino acid analyzer (120A) or on a model 476A according to the instructions of the manufacturer (Applied Biosystems, Foster City, Calif., U.S.A.).

Figure 2:
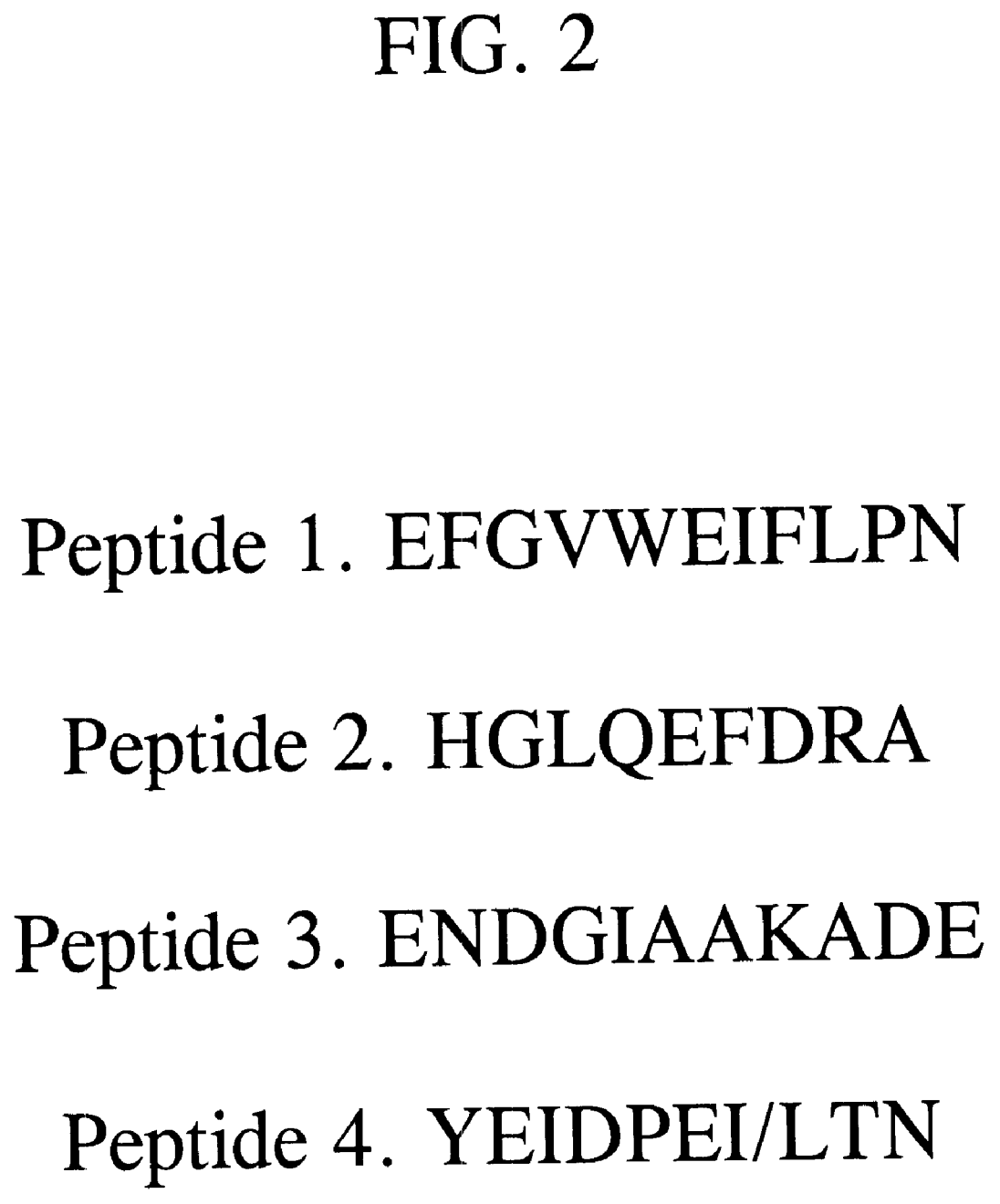

Four of the peptides sequenced gave easily interpretable sequences (FIG. 2). A data base search revealed that these four peptides displayed similarity to starch branching enzymes and interestingly, the peptides were more related to starch branching enzyme II from other plant species than to starch branching enzyme I from potato.

Construction of Oligonucleotides Encoding Peptides 1 and 2

Degenerated oligonucleotides encoding peptide 1 and peptide 2 were synthesized as forward and reverse primers, respectively:

Oligonucleotide 1: 5'-gtaaaacgacggccagtTTYGGNGTNTGGGARATHTT-3' (Residues 2 to 8 of peptide 1)

Oligonucleotide 2: 5'-aattaaccctcactaaagggCKRTCRAAYTCYTGIARNCC-3'(Residues 2 to 8 of peptide 2, reversed strand)

wherein

H is A, C or T, I is inosine; K is G or T; N is A, C, G or T; R is A or G; Y is C or T; bases in lower case were added as tag sequences.

Purification of mRNA from Potato Tuber, Synthesis of cDNA and PCR Amplification of a cDNA Fragment Corresponding to Potato Starch Branching Enzyme II Total RNA from mature potato tubers (*S. tuberosum* cv. Amanda) was isolated as described (Logemann et al. 1987). First strand cDNA was synthesized using 2 $\mu$g of total RNA and 60 pmol of oligo-$dT_{30}$ as downstream primer. The primer was annealed to the polyA of the mRNA at 60° C. for 5 min. The extension of the cDNA was performed according to the technical manual of the manufacturer using the Riboclone® cDNA Synthesis System M-MLV (H-) (Promega).

cDNA encoding the novel starch branching enzyme II according to the invention was amplified in a Perkin-Elmer GeneAmp® 9600 PCR thermocycler (Perkin-Elmer Cetus Instruments, Conn., U.S.A) using the two degenerate primers designed from the peptides 1 and 2 (see above) under the following conditions: 1 mM dNTP, 1 $\mu$M of each primer and an alicot of the cDNA described above in a total reaction volume of 20 $\mu$l with 1×AmpliTaq® buffer and 0.8 U AmpliTaq® (Perkin-Elmer Cetus). The cycling conditions were: 96° C. for 1', 80° C. while the enzyme was added as a hotstart (approximately 15'), an unintended drop to 25° C., five cycles of 94° C. for 20", 45° C. for 1', ramp to 72° C. for 1' and 72° C. for 2', and 30 cycles of 94° C. for 5", 45° C. for 30", and 72° C. for (2'+2" per cycle) and completed with 72° C. for 10' prior to chilling to 4° C.

A sample of this reaction (0.1 $\mu$l) was reamplified using the cycling conditions: 960° C. for 1', 80° C. while the enzyme was added as a hotstart (approximately 5'), five cycles of 94° C. for 20", 45° C. for 1', and 72° C. for 2', and 25 cycles of 94° C. for 51", 45° C. for 30", and 72° C. for (2'+2" per cycle) and completed with 72° C. for 10' prior to chilling to 4° C. After completion of the PCR amplification, the reaction was loaded on a 1.5% Seakem® agarose gel (FMC Bioproducts, Rockland, Me., U.S.A). After electrophoresis and staining with ethidium bromide a major band with an apparent size of 1500 bp was excised and the fragment was eluted by shaking in water (200 $\mu$l) for 1 h. This fragment was used as template in sequencing reactions after reamplification using primers corresponding to the tag sequences (in oligonucleotides 1 and 2), purification by agarose gel electrophoresis as above and extraction from the gel using the Qiaex® gel extraction kit according to the manufacturer's instructions (DIAGEN GmbH, Hilden, Germany). The sequencing reactions were done using the DyeDeoxy® Terminator Cycle Sequencing kits (Perkin-Elmer Cetus Instruments) using tag sequences and internal primers. The sequencing reaction were analyzed on an Applied Biosystems 373A DNA sequencer according to the manufacturer's protocols. The sequence wets edited and comprised 1393 bp.

To complete the determination of the sequence of starch branching enzyme II, the 5' and 3' ends of the full length cDNA were amplified from the same total RNA as above using rapid amplification of cDNA ends, RACE, methodology with specific primers from the 1393 bp sequence. In the 3' end amplification, an oligo $T_{29}G$ primer was used against the poly A tail and in the 5' end, the 5'/3' RACE kit from Boehringer Mannheim (Cat. No. 1734792) was used. The fragments from these amplifications were sequenced in the same way as above using internal and end primers. The sequences from the two ends were aligned together with the 1393 base pairs to give a composite full length cDNA sequence. Primers were designed from this sequence to amplify the whole coding region in one part. Partial sequencing of the amplified coding cDNA confirmed the presence of a cDNA corresponding to the composite sequence. The full length cDNA is 3074 bp and the translated sequence comprises 878 amino acids. The mature protein comprises 830 amino acids.

Comparisons of the consensus sequence with the EMBL and GenBank databases showed 68% identity to potato starch branching enzyme I and about 80% identity to starch branching enzyme II from other plant species. The present inventors therefore denote the enzyme encoded by the new branching enzyme sequence potato starch branching enzyme II.

Transformation of Potato Plants

The isolated full length cDNA of potato starch branching enzyme II and other functionally active fragments in the range of 50-3074 bp are cloned in reverse orientation behind promoters active in potato tubers. By the term "functionally active" is meant fragments that will affect the amylose/amylopectin ratio in potato starch. The DNA and amino acid sequence of SBE II according to the invention as well as one fragment of the DNA and corresponding amino acid sequence are shown in SEQ ID No. 1 and 2, respectively.

The promoters are selected from, for example, the patatin promoter, the promoter from the potato granule-bound starch synthase I gene or promoters isolated from potato starch branching enzymes I and II genes.

The constructs are cloned by techniques known in the art either in a binary Ti-plasmid vector suitable for transformation of potato mediated by *Agrobacterium tumefaciens,* or in a vector suitable for direct transformation using ballistic techniques or electroporation. It is realized that the sense (see below) and antisense constructs must contain all necessary regulatory elements.

Transgenic potato plants transcribe the inverse starch branching enzyme II construct specifically in tubers, leading to antisense inhibition of the enzyme. A reduction and changed pattern of the branching of amylopectin as well as a changed amylose/amylopectin ratio thereby occur in tuber starch.

The antisense construct for potato starch branching enzyme II is also used in combination with antisense constructs for potato starch branching enzyme I, for potato granule-bound starch synthase II, for potato soluble starch synthases II and III, for potato starch disproportionating enzyme (D-enzyme) or for potato starch debranching enzyme to transform potato to change the degree of branching of amylopectin and the amylose/amylopectin ratio. This gives now and valuable raw material to the starch processing industry.

The full-length cDNA sequence encoding the enzyme is, in different constructs, cloned in sense orientation behind one or more of the promoters mentioned above, and the constructs are transferred into suitable transformation vectors as described above and used for the transformation of potato. Regenerated transformed potato plants will produce an excess of starch branching enzyme II in the tubers leading to an increased degree and changed pattern of branching of amylopectin or to inhibition of transcription of endogenous starch branching enzyme II transcription due to co-suppression, resulting in a decreased branching of amylopectin.

REFERENCES

Müller-Röber, B., Koβmann, J., (1994) Approaches to influence starch quantity and starch quality in transgenic plants. Plant Cell Environm. 17, 601–613.

Martin, C., Smith, A. (1995) Starch Biosynthesis. Plant Cell 7, 971–985.

Laemmli, U. K. (1979) Cleavage of structural proteins during assembly of the head of bacteriophage T4. Nature 227, 680–685.

Logemann, J., Schell, J. and Willmitzer, L. (1987) Improved method for the isolation of RNA from plant tissues. Anal. Biochem. 163, 16–20.

Rosenfeld, J., Capdeville, J, Guillemot, J. C., Ferrara, P. (1992) In-gel digestion of proteins for internal sequence analysis after one- or two-dimensional gel electrophoresis. Anal. Biochem. 203, 173–179.

Visser, R. G. F., Jacobsen, E. (1993) Towards modifying plants for altered starch content and composition. TibTech 11, 63–68.

We claim:

1. An isolated DNA sequence encoding starch branching enzyme II (SBE II) of potato, said DNA sequence comprising the nucleotide sequence as shown in SEQ ID No. 1, or variants of said DNA sequence resulting from the degeneracy of the genetic code.

2. Fragments of the isolated DNA sequence as shown in SEQ ID No. 1 and said fragments encoding starch branching enzyme II (SBE II) of potato, which fragments are capable of affecting the amylose/amylopectin ratio in potato starch as well as reducing or changing the pattern of the branching of amylopectin.

3. Fragments according to claim 2 comprising 50-3074 bp of the nucleotide sequence as shown in SEQ ID No. 1, or variants of said fragments resulting from the degeneracy of the genetic code.

4. A fragment according to claim 2, comprising the nucleotide sequence as shown in SEQ ID No. 2.

5. A vector comprising the whole or a functionally active part of the isolated DNA sequence according to claim 1 operably linked to regulatory elements active in potato, said part being of a length sufficient to affect the amylose/amylopectin ratio in potato starch.

6. A vector comprising the whole or a functionally active part of the fragment according to claim 2 operably linked to regulatory elements active in potato, said part being of a length sufficient to affect the amylose/amylopectin ratio in potato starch.

7. A vector comprising the whole or a functionally active part of the fragment according to claim 3 operably linked to regulatory elements active in potato, said part being of a length sufficient to affect the amylose/amylopectin ratio in potato starch.

8. A vector comprising the whole or a functionally active part of the fragment according to claim 4 operably linked to regulatory elements active in potato, said part being of a length sufficient to affect the amylose/amylopectin ratio in potato starch.

9. A process for the production of transgenic potatoes with either an increased or a decreased degree of branching of amylopectin starch, comprising the following steps:

a) transfer and incorporation of a vector according to claim 5 into the genome of a potato cell, and b) regeneration of intact, whole plants from the transformed cells.

10. A transgenic potato obtainable by the process according to claim 9.

11. A process for isolating starch or starch proteins from the transgenic potato of claim 10, comprising:

i) homogenizing said transgenic potato to create a homogenate;

ii) obtaining a juice fraction from said homogenate;

iii) allowing the starch to sediment from said juice fraction; and iv) collecting the starch.

* * * * *